(12) United States Patent
Karasawa

(10) Patent No.: US 8,197,412 B2
(45) Date of Patent: Jun. 12, 2012

(54) ULTRASONIC DIAGNOSTIC APPARATUS

(75) Inventor: Hiroyuki Karasawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 440 days.

(21) Appl. No.: 12/467,774

(22) Filed: May 18, 2009

(65) Prior Publication Data

US 2009/0292207 A1  Nov. 26, 2009

(30) Foreign Application Priority Data

May 26, 2008 (JP) ................................. 2008-136478

(51) Int. Cl.
*A61B 8/00* (2006.01)
*G06K 9/20* (2006.01)

(52) U.S. Cl. ........ 600/447; 600/438; 600/442; 600/443; 382/107; 382/128

(58) Field of Classification Search .................. 600/437, 600/447, 443, 442, 438, 439; 382/107, 236, 382/128–133
See application file for complete search history.

(56) References Cited

U.S. PATENT DOCUMENTS

| | | | | |
|---|---|---|---|---|
| 5,357,962 A | * | 10/1994 | Green | 600/443 |
| 5,429,137 A | * | 7/1995 | Phelps et al. | 600/455 |
| 5,638,820 A | * | 6/1997 | Chen et al. | 600/437 |

FOREIGN PATENT DOCUMENTS

| | | |
|---|---|---|
| JP | 59-212791 A | 12/1984 |
| JP | 5-329159 A | 12/1993 |
| JP | 2007-7045 A | 1/2007 |

* cited by examiner

*Primary Examiner* — Long V. Le
*Assistant Examiner* — Katherine Fernandez
(74) *Attorney, Agent, or Firm* — Sughrue Mion, PLLC

(57) ABSTRACT

An ultrasonic diagnostic apparatus in which degradation in calculation accuracy and increase in calculation time can be prevented while an ultrasonic image with high resolving power is generated by using appropriate acoustic velocities for respective regions within an object. The apparatus includes: a transmitting and receiving unit for processing reception signals; a reception control unit for performing focusing processing based on acoustic velocity values to generate a sound ray signal; an image generating unit for generating an image signal based on the sound ray signal; a focusing determining unit for determining a degree of beam focusing in the focusing processing with respect to plural first regions; and an acoustic velocity value correcting unit for obtaining acoustic velocity values with respect to the plural first regions and further obtaining acoustic velocity values with respect to plural second regions segmented in smaller regions than the plural first regions.

9 Claims, 5 Drawing Sheets

ULTRASONIC DIAGNOSTIC APPARATUS

BACKGROUND OF THE INVENTION

1. Field of the Invention

The present invention relates to an ultrasonic diagnostic apparatus for imaging organs within a living body and so on by transmitting and receiving ultrasonic waves to generate ultrasonic images to be used for diagnoses.

2. Description of a Related Art

In medical fields, various imaging technologies have been developed for observing inside of an object to be inspected so as to make diagnoses. Especially, ultrasonic imaging for acquiring interior information of the object by transmitting and receiving ultrasonic waves enables image observation in real time and provides no exposure to radiation unlike other medical image technologies such as X-ray photography or RI (radio isotope) scintillation camera. Accordingly, ultrasonic imaging is utilized as an imaging technology at a high level of safety in a wide range of departments including not only the fetal diagnosis in obstetrics, but gynecology, circulatory system, digestive system, and so on.

The principle of ultrasonic imaging is as below. Ultrasonic waves are reflected at a boundary between regions with different acoustic impedances like a boundary between structures within the object. Therefore, by transmitting ultrasonic beams into the object such as a human body, receiving ultrasonic echoes generated within the object, and obtaining reflection points where the ultrasonic echoes are generated and reflection intensity, outlines of structures (e.g., internal organs, diseased tissues, and so on) existing within the object can be extracted.

The acoustic impedance is a constant intrinsic to a material as expressed by equation (1), and the unit of MRayl (mega Rayl) is generally used therefor and 1 MRayl=1×10$^6$ kg·m$^{-2}$·s$^{-1}$.

$$Z = \rho \cdot C \quad (1)$$

where $\rho$ represents density of an acoustic medium and $C$ represents acoustic velocity within the acoustic medium.

Further, given that the acoustic impedance of the first medium is $Z_1$ and the acoustic impedance of the second medium adjacent to the first medium is $Z_2$, the vertical reflectance R of ultrasonic waves at the interface between the first medium and the second medium is given by the following equation (2).

$$R = (Z_2 - Z_1)/(Z_2 + Z_1) \quad (2)$$

Generally, an ultrasonic image is generated based on the intensity of ultrasonic waves reflected at the respective sample points within the object. Since the acoustic velocities are different depending on tissues within the object, there are problems that defocusing occurs in reception focusing processing and/or transmission focusing processing, the resolving power becomes lower, and image blurring occurs.

As related technologies, Japanese Patent Application Publication JP-A-5-329159 discloses an ultrasonic diagnostic apparatus in which images in the optimum focused state can be obtained consistently regardless of variations in conditions of acoustic velocity distribution within the object and so on. The ultrasonic diagnostic apparatus includes transmission focusing means for performing transmission focusing by sequentially selecting plural transmission focusing patterns and determining driving timings of plural ultrasonic vibrators according to the selected transmission focusing patterns, reception focusing means for performing reception focusing on echo signals outputted from the plural ultrasonic vibrators by providing delays according to plural reception focusing patterns in time sequence or at the same time, signal processing means for generating image data based on the echo signals reception-focused by the reception focusing means, image data storage means for storing plural image data using plural combinations of transmission focusing patterns and reception focusing patterns for the same part of the object, focusing evaluation means for selecting image data in the optimum focused state by comparing predetermined feature quantities of the respective image data of the plural image data stored in the image data storage means, and image forming means for forming tomographic images based on the image data selected by the focusing evaluation means.

Japanese Patent Application Publication JP-A-59-2127 91 discloses an ultrasonic imaging system of aperture type for automatically focusing on a part desired to be observed. According to the ultrasonic imaging system, all acoustic velocity setting values are determined such that the sharpness of the image within a small region of interest is the maximum, and then, an acoustic correction value for a partial aperture is determined such that the image within the small region due to the partial aperture has the same correlation value with the first obtained image within the small region, and the acoustic correction values corresponding to the respective parts of the entire aperture are determined while the partial aperture of interest is moved and varied in size to cover the entire aperture.

Japanese Patent Application Publication JP-P2007-7045A discloses realization of estimation of the acoustic velocity of a living body in an ultrasonic diagnostic apparatus. The ultrasonic diagnostic apparatus includes an ultrasonic probe having arranged plural vibrators, a transmission circuit for transmitting ultrasonic waves to the object via the ultrasonic probe, a reception circuit for receiving echo signals from the object via the ultrasonic probe, an intensity distribution generating unit for generating plural ultrasonic intensity distributions at different acoustic velocities set for delay control.

As disclosed in these documents, it is possible to obtain the optimum acoustic velocities in the respective regions within the object. However, if the optimum acoustic velocities are obtained in the small regions, there are problems that the number of data for obtaining the acoustic velocities is reduced and the calculation accuracy becomes lower, and the number of regions is increased and the time for calculation is increased. Further, if an image is formed by using acoustic velocities different with respect to each region, artifacts would occur at boundaries between regions.

SUMMARY OF THE INVENTION

The present invention has been achieved in view of the above-mentioned problems. A purpose of the present invention is to provide an ultrasonic diagnostic apparatus in which degradation in calculation accuracy and increase in calculation time can be prevented while an ultrasonic image with high resolving power is generated by using appropriate acoustic velocities for respective regions within the object.

In order to accomplish the above-mentioned purpose, an ultrasonic diagnostic apparatus according to one aspect of the present invention includes: a transmitting and receiving unit for supplying drive signals to plural ultrasonic transducers to transmit ultrasonic waves to an object to be inspected, and processing reception signals outputted from the plural ultrasonic transducers which have received ultrasonic echoes reflected by the object; reception control means for performing focusing processing by matching phases of the reception signals outputted from the transmitting and receiving unit according to plural delay amounts set based on acoustic velocity values within the object to generate a sound ray signal along a reception direction of the ultrasonic echoes; image generating means for generating an image signal representing an ultrasonic image based on the sound ray signal generated by the reception control means; focusing determining means for determining a degree of beam focusing in the focusing processing with respect to plural first regions within the ultrasonic image based on the sound ray signal generated by the reception control means; and acoustic velocity value correcting means for obtaining acoustic velocity values with respect to the plural first regions according to a determination result of the focusing determining means and further obtaining acoustic velocity values with respect to plural second regions segmented in smaller regions than the plural first regions, such that the reception control means generates the sound ray signal based on the acoustic velocity values obtained with respect to the plural second regions and the image generating means generates the image signal based on the sound ray signal.

According to the one aspect of the present invention, by obtaining acoustic velocity values with respect to the plural first regions according to a determination result of the focusing determining means and further obtaining acoustic velocity values with respect to plural second regions segmented in smaller regions than the plural first regions, the degradation in calculation accuracy and increase in calculation time can be prevented while an ultrasonic image with high resolving power is generated by using appropriate acoustic velocities for respective regions within the object.

DESCRIPTION OF THE PREFERRED EMBODIMENTS

Hereinafter, embodiments of the present invention will be described in detail with reference to the drawings.

Figure 1:
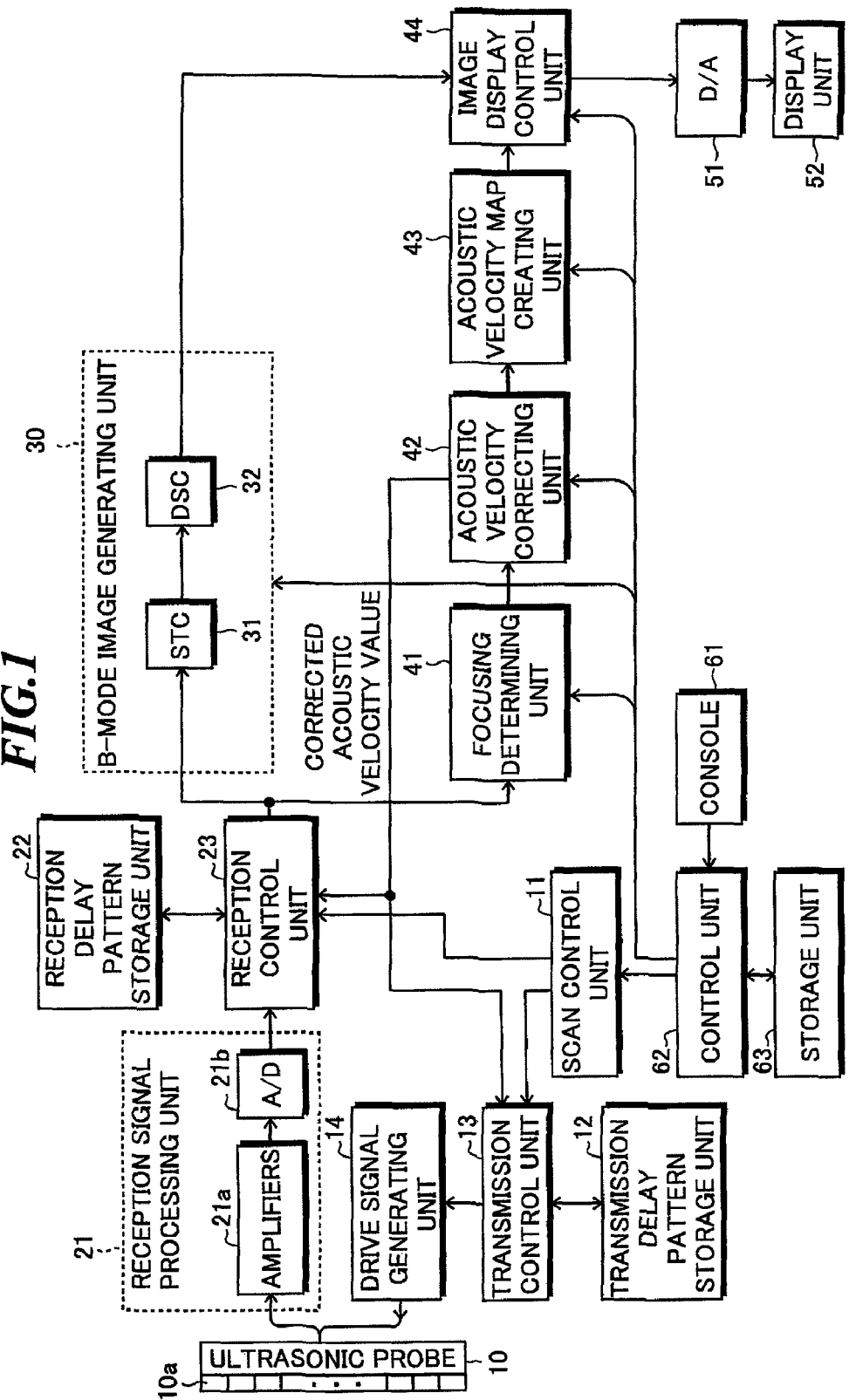
FIG. 1 is a block diagram showing a configuration of an ultrasonic diagnostic apparatus according to one embodiment of the present invention.

FIG. 1 is a block diagram showing a configuration of an ultrasonic diagnostic apparatus according to one embodiment of the present invention. The ultrasonic diagnostic apparatus includes an ultrasonic probe 10, a scan control unit 11, a transmission delay pattern storage unit 12, a transmission control unit 13, a drive signal generating unit 14, a reception signal processing unit 21, a reception delay pattern storage unit 22, a reception control unit 23, a B-mode image generating unit 30, a focusing determining unit 41, an acoustic velocity value correcting unit 42, an acoustic velocity map creating unit 43, an image display control unit 44, a D/A converter 51, a display unit 52, a console 61, a control unit 62, and a storage unit 63.

The ultrasonic probe 10 includes plural ultrasonic transducers 10a forming a one-dimensional or two-dimensional transducer array. These ultrasonic transducers 10a transmit ultrasonic waves based on applied drive signals, and receive propagating ultrasonic echoes to output reception signals.

Each ultrasonic transducer includes a vibrator having electrodes formed on both ends of a material having a piezoelectric property (piezoelectric material) such as a piezoelectric ceramic represented by PZT (Pb (lead) zirconate titanate), a polymeric piezoelectric element represented by PVDF (polyvinylidene difluoride), or the like. When a pulsed or continuous wave voltage is applied to the electrodes of the vibrator, the piezoelectric material expands and contracts. By the expansion and contraction, pulse or continuous wave ultrasonic waves are generated from the respective vibrators, and an ultrasonic beam is formed by synthesizing these ultrasonic waves. Further, the respective vibrators expand and contract by receiving the propagating ultrasonic waves to generate electric signals. These electric signals are outputted as reception signals of ultrasonic waves.

The scan control unit 11 sequentially sets the transmission directions of ultrasonic beams and the reception directions of ultrasonic echoes. The transmission delay pattern storage unit 12 has stored plural transmission delay patterns to be used when ultrasonic beams are formed. The transmission control unit 13 selects a transmission delay pattern from among the plural transmission delay patterns stored in the transmission delay pattern storage unit 12 according to the transmission direction set by the scan control unit 11, and sets delay times to be provided to drive signals of the plural ultrasonic transducers 10a based on the selected transmission delay pattern. Alternatively, the transmission control unit 13 may set delay times such that the ultrasonic waves simultaneously transmitted from the plural ultrasonic transducers 10a reach the entire imaging region of the object.

The drive signal generating unit 14 includes plural pulsers corresponding to the plural ultrasonic transducers 10a, for example. According to the delay times set by the transmission control unit 13, the drive signal generating unit 14 supplies drive signals to the ultrasonic probe 10 such that the ultrasonic waves transmitted from the plural ultrasonic transducers 10a form an ultrasonic beam, or supplies drive signals to the ultrasonic probe 10 such that the ultrasonic waves simultaneously transmitted from the plural ultrasonic transducers 10a reach the entire imaging region of the object.

The reception signal processing unit 21 includes plural preamplifiers 21a and plural A/D converters 21b corresponding to the plural ultrasonic transducers 10a. The reception signals outputted from the respective ultrasonic transducers 10a are amplified in the amplifiers 21a and the analog signals outputted from the amplifiers 21a are converted into digital reception signals by the A/D converters 21b. The A/D converters 21b output the digital reception signals to the reception control unit 23.

The reception delay pattern storage unit 22 has stored plural reception delay patterns to be used when focusing processing is performed on the reception signals outputted from the plural ultrasonic transducers 10a. The reception control unit 23 selects a reception delay pattern from among the plural reception delay patterns stored in the reception delay pattern storage unit 22 according to the reception direction set by the scan control unit 11, and performs reception focusing processing by providing delays to the reception signals based on the selected reception delay pattern and the acoustic velocity within the object, and adding the reception signals. Further, transmission focusing processing may be performed based on the reception signals. By the focusing processing, a sound ray signal, in which the focus of the ultrasonic echoes is narrowed, is formed. Furthermore, the reception control unit 23 performs envelope detection processing on the formed sound ray signal.

Here, the delay amounts of reception signals are determined based on the acoustic velocity within the object. Generally, the acoustic velocity value C0 within a living body is set to 1530 m/s or 1540 m/s, however, actually, the acoustic velocity values vary depending on tissues within a living body. Accordingly, the acoustic velocity value C1 within the object is set and delay amount D0(j) in the reception delay pattern is multiplied by (C0/C1), and thereby, plural delay amounts D1(j)=(C0/C1)·D0(j) are determined (j=1, 2, ..., L). Here, L is the number of ultrasonic transducers to be used.

The B-mode image generating unit 30 generates a B-mode image signal as tomographic image information on tissues within the object based on the sound ray signal outputted from the reception control unit 23. For the purpose, the B-mode image generating unit 30 includes an STC (sensitivity time control) part 31, and a DSC (Digital Scan Converter) 32.

The STC part 31 performs corrects attenuation by distance on the sound ray signal outputted from the reception control unit 23 according to the depths of the reflection positions of ultrasonic waves. The DSC 32 converts (raster-converts) the sound ray signal corrected by the STC part 31 into an image signal that follows the normal scan system of television signals and performs necessary image processing such as gradation processing to generate a B-mode image signal.

The control unit 62 controls the focusing determining unit 41 and the acoustic velocity value correcting unit 42 to determine the degree of beam focusing and correct set acoustic velocities in parallel with the generation of the B-mode image signal by the B-mode image generating unit 30. The focusing determining unit 41 determines the degree of beam focusing in the focusing processing based on the sound ray signal outputted from the reception control unit 23 with respect to plural first regions within the ultrasonic image. The acoustic velocity value correcting unit 42 obtains acoustic velocity values with respect to the plural first regions according to the determination result of the focusing determining unit 41, and further obtains acoustic velocity values with respect to plural second regions which are segmented into smaller regions than the first regions, and thereby, corrects the acoustic velocity values.

The acoustic velocity values corrected by the acoustic velocity value correcting unit 42 are outputted to the reception control unit 23 and/or the transmission control unit 13. The reception control unit 23 generates the sound ray signal by correcting the delay amounts of the reception signals based on the corrected acoustic velocity values, and the B-mode image generating unit 30 generates the B-mode image signal based on the sound ray signal. Thereby, the accuracy in reception focusing processing is improved, and the image quality of the ultrasonic image is improved. Further, when transmission focusing processing (transmission beam forming) is performed, the transmission control unit 13 can correct the delay amounts of the drive signals based on the corrected acoustic velocity values. Thereby, accuracy in transmission focusing processing is improved, and the image quality of the ultrasonic image is further improved.

The acoustic velocity map creating unit 43 generates an image signal representing an acoustic velocity map for displaying the acoustic velocity distribution within the ultrasonic image based on the acoustic velocity values obtained by the acoustic velocity value correcting unit 42. The image display control unit 44 generates an image signal for display by selecting at least one of the ultrasonic image based on the B-mode image signal generated by the B-mode image generating unit 30 and the acoustic velocity map based on the image signal generated by the acoustic velocity map creating unit 43.

The D/A converter 51 converts the digital image signal outputted from the image display control unit 44 into an analog image signal. The display unit 52 includes a display device such as a CRT, LCD, or the like, and displays ultrasonic images based on the analog image signal.

The control unit 62 controls the scan control unit 11, the B-mode image generating unit 30, the focusing determining unit 41, and so on according to the operation of an operator using the console 61. In the embodiment, the scan control unit 11, transmission control unit 13, reception control unit 23, B-mode image generating unit 30, focusing determining unit 41 to image display control unit 44, and control unit 62 can be realized by a CPU and software (program), however, they may be formed by digital circuits or analog circuits. The software (program) is stored in the storage unit 63. As a recording medium in the storage unit 63, not only a built-in hard disk but also a flexible disk, MO, MT, RAM, CD-ROM, DVD-ROM, or the like may be used.

Next, the correction processing of acoustic velocity values in the ultrasonic diagnostic apparatus shown in FIG. 1 will be explained in detail.

Figure 2:
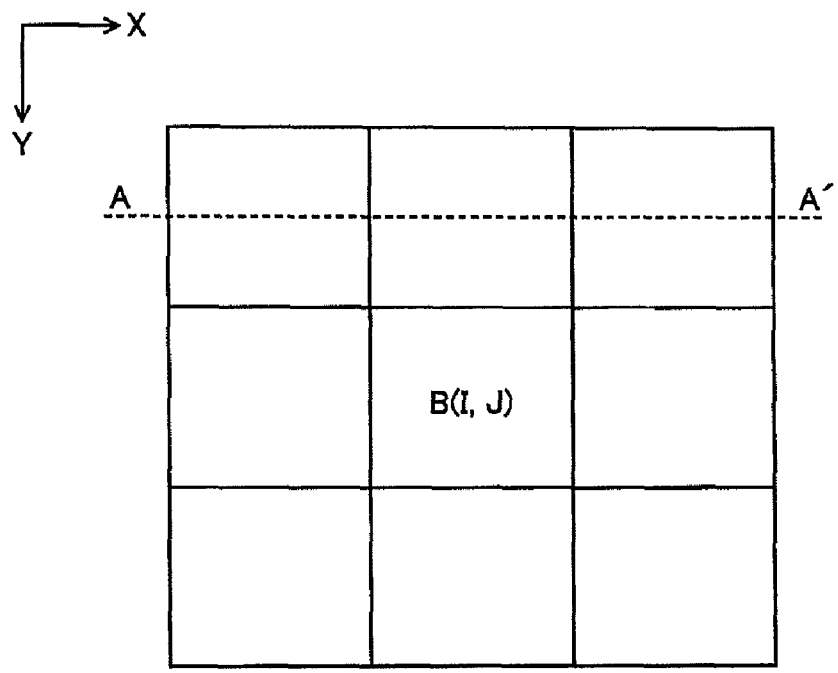
FIG. 2 shows plural first regions within an ultrasonic image.

First, the acoustic velocity value correcting unit 42 obtains acoustic velocity values with respect to plural first regions within an ultrasonic image of the object. FIG. 2 shows plural first regions within the ultrasonic image. In FIG. 2, X-axis indicates one arrangement direction of ultrasonic transducers and Y-axis indicates the depth direction of the object. As shown in FIG. 2, region B(I, J) in the I-th row and the J-th column is set within the ultrasonic image of the object (XY section), where I=1, 2, 3, and J=1, 2, 3.

Figure 3:
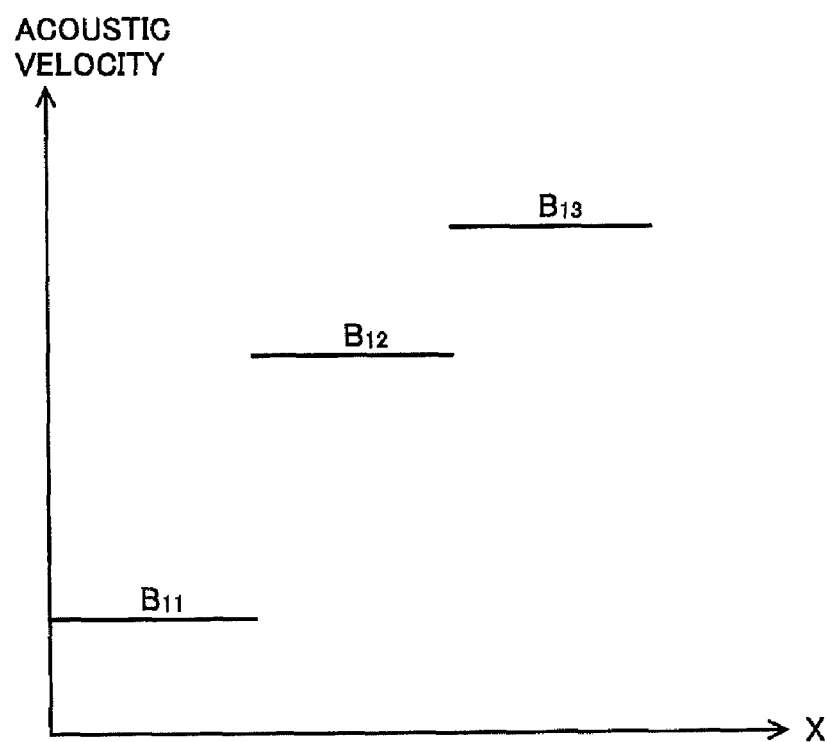
FIG. 3 shows acoustic velocity values obtained with respect to the first regions obtained along a set line.

FIG. 3 shows acoustic velocity values with respect to the first regions obtained along a set line. FIG. 3 shows acoustic velocity values $B_{11}$ to $B_{13}$ with respect to regions B(1, 1) to B(1, 3) obtained along line A-A' shown in FIG. 2. The acoustic velocity value $B_{IJ}$ with respect to the region B(I, J) is obtained in the following manner, for example. The acoustic velocity value correcting unit 42 shown in FIG. 1 estimates some acoustic velocity values Ci (I=1, 2, ...) with respect to the region B(I, J), and the reception control unit 23 performs focusing processing while sequentially setting focal points along the line substantially in parallel with the X-axis within the region B(I, J), and thereby, a series of sound ray signals are formed. The focusing determining unit 41 determines the degree of beam focusing in the focusing processing based on those sound ray signals, and thereby, the optimum acoustic velocity value $B_{IJ}$ with respect to the region B(I, J) can be obtained.

When the degree of beam focusing in focus processing is good, the one-dimensional image along the set line is sharply focused and the resolving power becomes good. For example, when the peak value of brightness becomes the maximum or the ratio of high-frequency component to middle-frequency component in the spatial frequency becomes the maximum, the degree of beam focusing is determined to be the maximum. Note that the acoustic velocity value $B_{IJ}$ with respect to the region B(I, J) does not represent the acoustic velocity value in the region B(I, J) itself, but averagely represents the acoustic velocity values in the paths between the ultrasonic transducers used for generating the ultrasonic image of the region B(I, J) and the region B(I, J).

Figure 4:
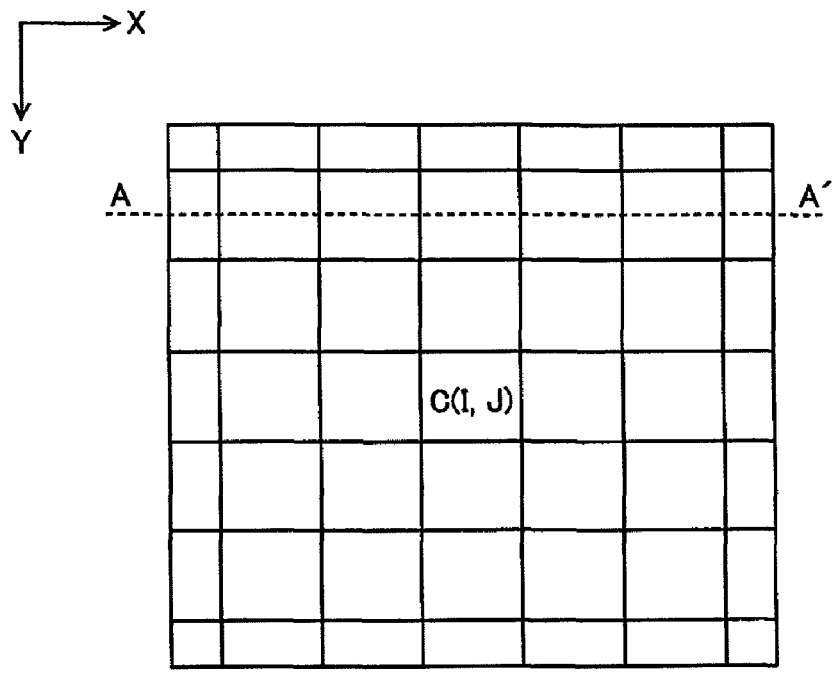
FIG. 4 shows plural second regions within the ultrasonic image.

Next, the acoustic velocity value correcting unit 42 obtains acoustic velocity values with respect to plural second regions which are segmented into smaller regions than the first regions within the ultrasonic image of the object. FIG. 4 shows the plural second regions within the ultrasonic image. As shown in FIG. 4, region C(I, J) in the I-th row and the J-th column is set within the ultrasonic image (XY section), where I=0, 1, ... , 6, and J=0, 1, ... , 6.

Figure 5:
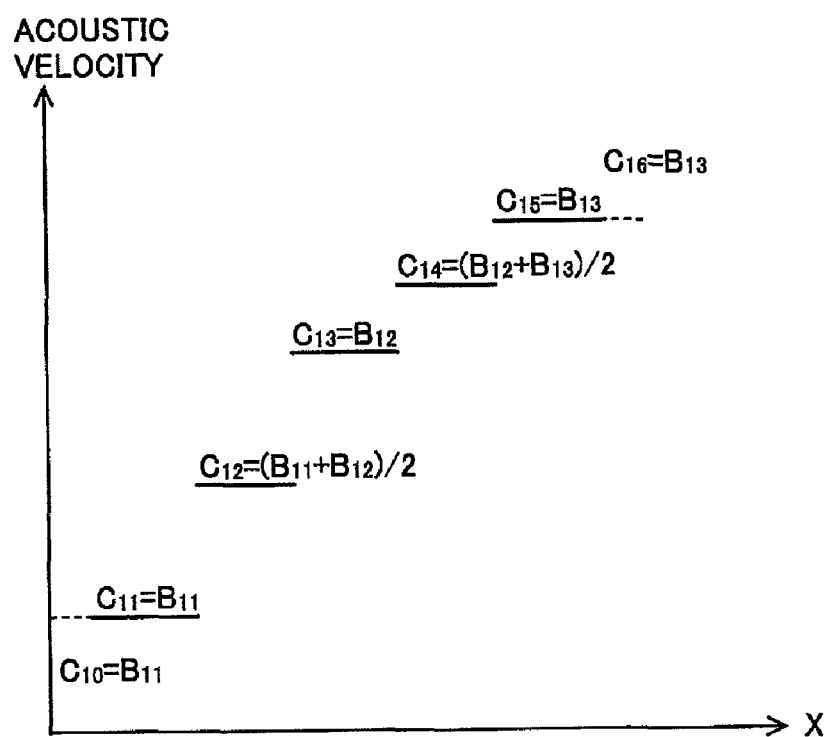
FIG. 5 shows acoustic velocity values obtained with respect to the second regions obtained along a set line.

FIG. 5 shows acoustic velocity values with respect to the second regions obtained along a set line. FIG. 5 shows acoustic velocity values $C_{10}$ to $C_{16}$ with respect to regions C(1, 0) to C(1, 6) obtained along line A-A' shown in FIG. 4. The acoustic velocity value $C_{IJ}$ with respect to the region C(I, J) is obtained in the following manner, for example. As shown in the following equations, as the acoustic velocity value $C_{IJ}$ with respect to the region C(I, J) contained in one of the regions B(I, J), the acoustic velocity value $B_{IJ}$ with respect to the region B(I, J) is used as it is.

$$C_{10}=B_{11}$$

$$C_{11}=B_{11}$$

$$C_{13}=B_{12}$$

$$C_{15}=B_{13}$$

$$C_{16}=B_{13}$$

Further, as shown in the following equations, as the acoustic velocity value $C_{IJ}$ with respect to the region C(I, J) across the plural regions B(I, J), the average value of the acoustic velocity values $B_{IJ}$ with respect to the regions B(I, J) is used.

$$C_{12}=(B_{11}+B_{12})/2$$

$$C_{14}=(B_{12}+B_{13})/2$$

In this way, by interpolating the acoustic velocity value $B_{IJ}$ with respect to the region B(I, J), acoustic velocity value $C_{IJ}$ with high accuracy can be obtained with respect to the region C(I, J).

Figure 6:
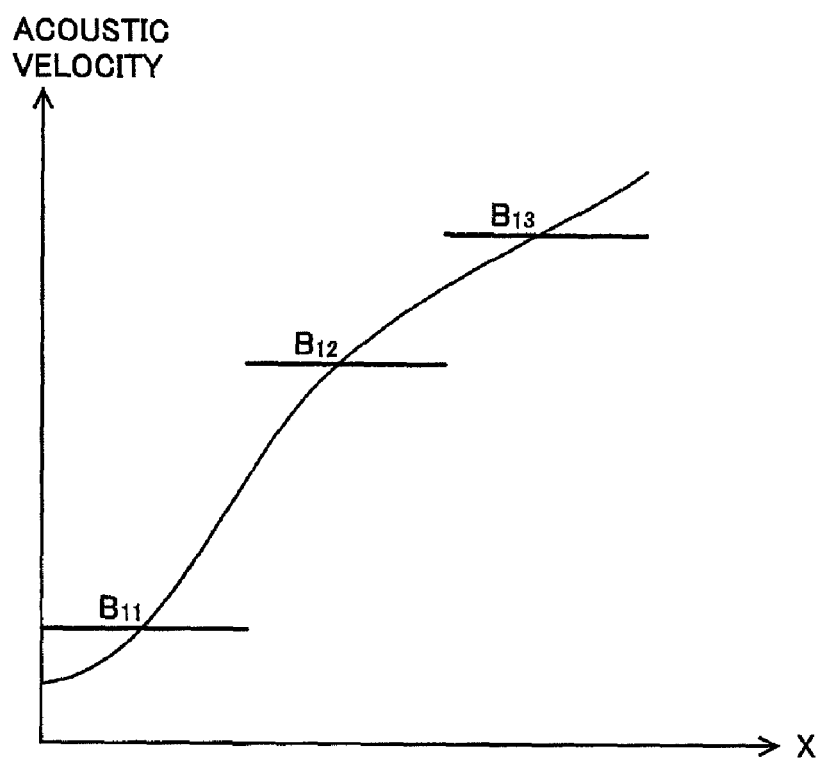
FIG. 6 shows an example in which smoothing processing is performed on acoustic velocity values along a set line.

Alternatively, by performing smoothing processing on the acoustic velocity values obtained with respect to the first regions, the acoustic velocity values with high accuracy can be obtained with respect to the second regions. FIG. 6 shows an example in which smoothing processing is performed on acoustic velocity values along a set line. In this example, by performing smoothing processing on acoustic velocity values $B_{11}$ to $B_{13}$ obtained with respect to regions B(1, 1) to B(1, 3) along line A-A' shown in FIG. 2, continuous acoustic velocities are obtained with respect to the second regions.

Figure 7:
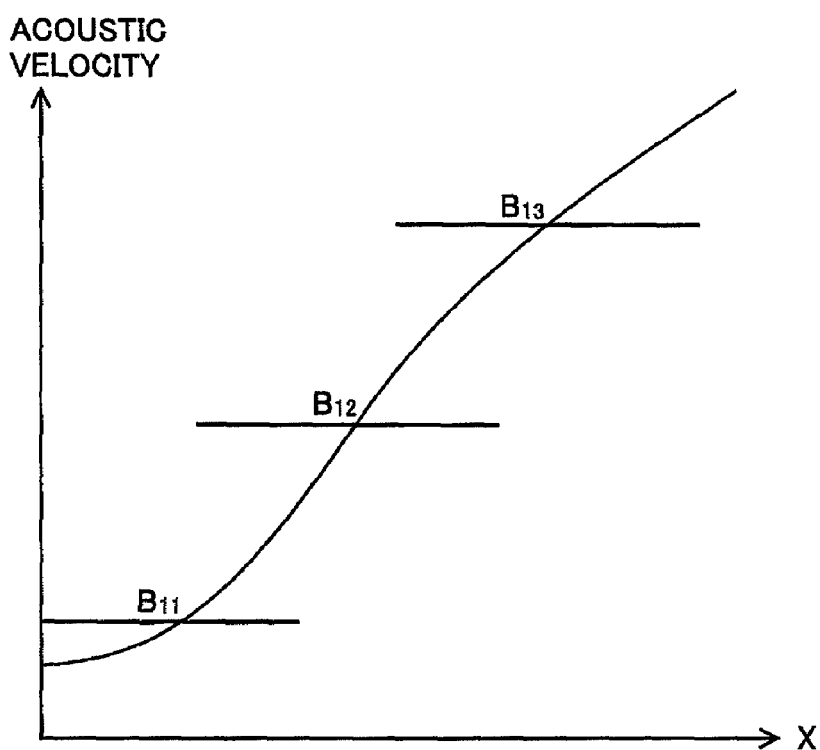
FIG. 7 shows another example in which smoothing processing is performed on acoustic velocity values along a set line.

FIG. 7 shows another example in which smoothing processing is performed on acoustic velocity values along a set line. In this example, the plural first regions B(I, J) are set to have overlapping parts with each other, and, by performing smoothing processing on acoustic velocity values $B_{11}$ to $B_{13}$ obtained with respect to regions B(1, 1) to B(1, 3) along line A-A' shown in FIG. 2, continuous acoustic velocities are obtained with respect to the second regions.

In the above-mentioned manner, it is desirable that the number of first regions is equal to or more than 4 (=2×2) and equal to or less than 100 (=10×10). Unless the number of first regions is equal to or more than 4, no effect of dividing regions can be expected. On the other hand, if the number of first regions is more than 100, the number of original data that can be used for obtaining the acoustic velocity value with respect to one region is reduced, and the acoustic velocity values have large variance and the S/N-ratio of the image signal is deteriorated. For example, it is considered that, if the number of original data that can be used for obtaining the acoustic velocity values is reduced to 1/100, it is considered that the S/N-ratio is deteriorated to about $(1/100)^{1/2}=1/10$.

In the embodiment, the acoustic velocity value correcting unit 42 can obtain the acoustic velocity values with respect to the second regions based on the reception signals obtained by one transmission. Further, the B-mode image generating unit 30 can generate the image signal based on the reception signals obtained by one transmission. According to the embodiment, reception focusing processing and/or transmission focusing processing can be performed with high accuracy and the accuracy of ultrasonic images can be improved.

On the basis of the sound ray signal generated by the reception control unit 23 shown in FIG. 1, the B-mode image generating unit 30 generates the B-mode image signal. In this regard, if ultrasonic waves are transmitted in the Y-axis direction as shown in FIG. 4 and ultrasonic echoes are received after time T passes, the depth Y of the reflection point is expressed by the following equation.

$$Y=CT/2$$

Here, if the acoustic velocity values C vary depending on the regions, there is a case where the order of receiving ultrasonic echoes and the order of depths in the ultrasonic image may be reversed. On this account, the acoustic velocity values to be used when focusing processing is performed by the reception control unit 23 vary depending on the regions, however, the acoustic velocity value C to be used when the B-mode image signal is generated by the B-mode image generating unit 30 is set to a fixed value. Thereby, artifacts occurring at boundaries between plural regions can be prevented.

Further, the acoustic velocity map creating unit 43 shown in FIG. 1 obtains the acoustic velocity values in the respective regions based on the acoustic velocity values with respect to the plural second regions obtained by the acoustic velocity value correcting unit 42.

Figure 8:
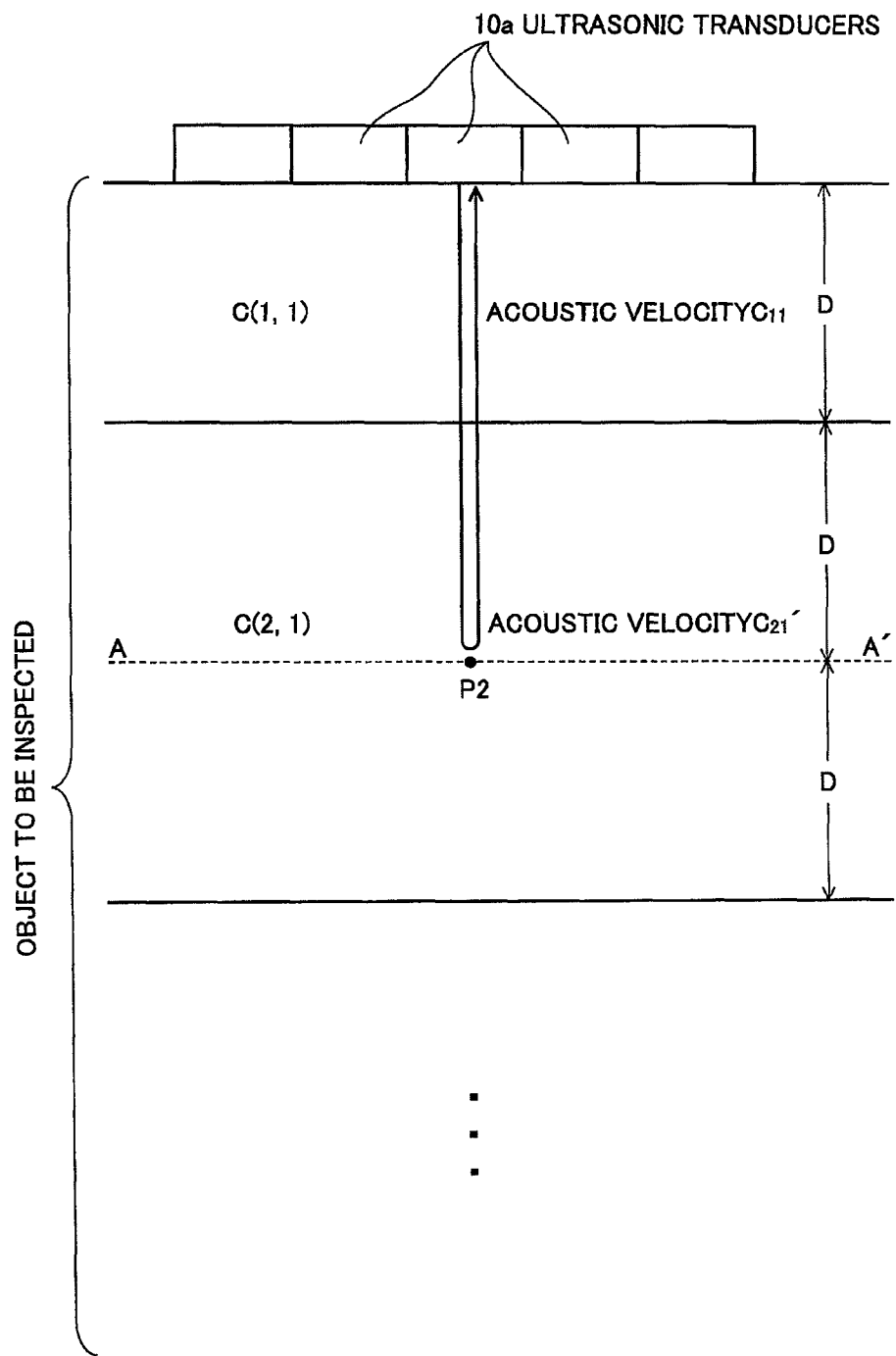
FIG. 8 is an enlarged view showing a part of the regions shown in FIG. 4.

FIG. 8 is an enlarged view showing a part of the regions shown in FIG. 4. In FIG. 8, regions C(1, 1), C(2, 1), ... are shown. It is assumed that the thickness of the region C(1, 1) is D, and the thicknesses of each of the regions C(2, 1), ... is 2D. The acoustic velocity value in the region C(1, 1) is equal to the acoustic velocity value $C_{11}$ obtained with respect to the region C(1, 1) in the above description.

Then, the case where ultrasonic waves are transmitted and received while focusing on the center point P2 of the region C(2, 1) will be considered. The ultrasonic waves transmitted from the ultrasonic transducers 10a pass through the region C(1, 1), are reflected at the center point P2 of the region C(2, 1), passes through the region C(1, 1) again, and are received by the ultrasonic transducers 10a.

Here, given that the acoustic velocity value in the region C(2,1) is $C_{21}'$ and the time from transmission to reception of ultrasonic waves by the ultrasonic transducers 10a is T2, the following equations hold.

$$T2=2\cdot D/C_{11}+2\cdot D/C_{21}'=4\cdot D/C_{21}$$

$$\therefore 1/C_{21}'=2/C_{21}-1/C_{11}$$

$$\therefore C_{21}'=C_{11}C_{21}/(2C_{11}-C_{21})$$

In the same manner, the acoustic velocity value $C_{31}'$ in the region C(3, 1) and so on are obtained. The acoustic velocity map creating unit 43 shown in FIG. 1 may further perform smoothing processing in the X-axis direction on the acoustic velocity values in the second regions obtained as described above to obtain highly continuous acoustic velocity values.

On the basis of the acoustic velocity values, the acoustic velocity map creating unit 43 generates an image signal representing an acoustic velocity map for displaying an acoustic velocity distribution within the ultrasonic image, and the acoustic velocity map is displayed on the display unit 52 based on the generated image signal.

The invention claimed is:

1. An ultrasonic diagnostic apparatus comprising:
   a transmitting and receiving unit for supplying drive signals to plural ultrasonic transducers to transmit ultrasonic waves to an object to be inspected, and processing reception signals outputted from said plural ultrasonic transducers which have received ultrasonic echoes reflected by the object;
   a reception control unit for performing focusing processing by matching phases of the reception signals outputted from said transmitting and receiving unit according to plural delay amounts set based on acoustic velocity values within the object to generate a sound ray signal along a reception direction of the ultrasonic echoes;
   an image generating unit for generating an image signal representing an ultrasonic image based on the sound ray signal generated by said reception control unit;
   a focusing determining unit for determining a degree of beam focusing in the focusing processing with respect to first regions within the ultrasonic image based on the sound ray signal generated by said reception control unit; and
   an acoustic velocity value correcting unit for obtaining first acoustic velocity values with respect to the first regions according to a determination result of said focusing determining unit and further obtaining second acoustic velocity values with respect to second regions segmented in smaller regions than the first regions, said acoustic velocity value correcting unit obtaining the second acoustic velocity values with respect to each second region, which is arranged across plural first regions, by performing at least one of interpolating processing and smoothing processing on the first acoustic velocity values, such that said reception control unit regenerates the sound ray signal based on the second acoustic velocity values and said image generating unit regenerates the image signal based on the regenerated sound ray signal.

2. The ultrasonic diagnostic apparatus according to claim 1, wherein said acoustic velocity value correcting means uses the first acoustic velocity values as the second acoustic velocity values with respect to each second region which is contained in one of the first regions.

3. The ultrasonic diagnostic apparatus according to claim 1, wherein said acoustic velocity value correcting means obtains the second acoustic velocity values having higher accuracy than that of the first acoustic velocity values.

4. The ultrasonic diagnostic apparatus according to claim 1, wherein said acoustic velocity value correcting unit obtains the first acoustic velocity values with respect to first regions having overlapping parts with each other.

5. The ultrasonic diagnostic apparatus according to claim 1, wherein the number of said first regions is within a range from 4 to 100.

6. The ultrasonic diagnostic apparatus according to claim 1, wherein said acoustic velocity value correcting unit obtains the second acoustic velocity values based on signals obtained by one transmission.

7. The ultrasonic diagnostic apparatus according to claim 1, wherein said image generating unit generates the image signal based on reception signals obtained by one transmission.

8. The ultrasonic diagnostic apparatus according to claim 1, further comprising:
   acoustic velocity map creating unit for generating an image signal representing an acoustic velocity map for displaying an acoustic velocity distribution within the ultrasonic image based on the second acoustic velocity values obtained by said acoustic velocity value correcting unit.

9. The ultrasonic diagnostic apparatus according to claim 1, wherein said first regions are segmented within said ultrasonic image.

* * * * *